(12) United States Patent
Bhatt et al.

(10) Patent No.: US 10,832,815 B2
(45) Date of Patent: Nov. 10, 2020

(54) MEDICAL SIDE EFFECTS TRACKING

(71) Applicant: International Business Machines Corporation, Armonk, NY (US)

(72) Inventors: Dhruv A. Bhatt, Indian Trail, NC (US); Bhargav Cheenepalli, Charlotte, NC (US); Kristin E. McNeil, Charlotte, NC (US); Nitaben A. Patel, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 731 days.

(21) Appl. No.: 15/598,607

(22) Filed: May 18, 2017

(65) Prior Publication Data

US 2018/0336318 A1 Nov. 22, 2018

(51) Int. Cl.
*G16H 40/63* (2018.01)
*G16H 20/00* (2018.01)
(Continued)

(52) U.S. Cl.
CPC ............ *G16H 40/63* (2018.01); *G16H 20/00* (2018.01); *G16H 50/20* (2018.01); *G16H 50/30* (2018.01); *G16H 50/50* (2018.01)

(58) Field of Classification Search
CPC ........ G16H 40/63; G16H 50/20; G16H 20/00; G16H 50/50; G16H 50/30
See application file for complete search history.

(56) References Cited

U.S. PATENT DOCUMENTS

| 7,730,063 B2 | 6/2010 | Eder |
| 8,260,631 B2 | 9/2012 | Morita et al. |

(Continued)

FOREIGN PATENT DOCUMENTS

WO 9850873 A1 11/1998

OTHER PUBLICATIONS

X. Jiang, et al., "A patient-driven adaptive prediction technique to improve personalized risk estimation for clinical decision support", Apr. 4, 2012, J Am Med Inform Assoc 2012;19:e137ee144, 8 pages.
(Continued)

*Primary Examiner* — Eliza A Lam
(74) *Attorney, Agent, or Firm* — Ryan Lewis; SVL IPLaw Edell, Shapiro & Finnan, LLC (57) ABSTRACT

According to one embodiment of the present invention, a system for monitoring medical events for adverse effects includes at least one processor. The processor may be configured to identify one or more medical events within patient medical information by applying first analytics to the medical information. The medical information may include unstructured information. The processor is further configured to determine adverse effects of the identified medical events and corresponding time intervals of occurrence by applying second analytics to medical reference information, wherein effect information includes the identified medical events, determined adverse effects, and corresponding time intervals of occurrence. In addition, the processor is configured to determine from the effect information any adverse effects for a patient and the corresponding time intervals of occurrence. Finally, the processor is configured to notify a user of the determined adverse effects prior to initiation of the corresponding time intervals of occurrence.

16 Claims, 5 Drawing Sheets

(51) Int. Cl.
*G16H 50/20* (2018.01)
*G16H 50/30* (2018.01)
*G16H 50/50* (2018.01)

(56) References Cited

U.S. PATENT DOCUMENTS

| | | | |
|---|---|---|---|
| 8,401,870 B2 | 3/2013 | Whelchel et al. | |
| 8,595,028 B2 | 11/2013 | Green, III et al. | |
| 8,751,495 B2 | 6/2014 | Chung et al. | |
| 8,990,135 B2 | 3/2015 | Syed et al. | |
| 9,414,776 B2 | 8/2016 | Sillay et al. | |
| 2007/0226175 A1* | 9/2007 | Resnic | G06F 19/00 |
| 2010/0070300 A1 | 3/2010 | Anderson et al. | |
| 2011/0295621 A1 | 12/2011 | Farooq et al. | |
| 2013/0244892 A1* | 9/2013 | Adourian | G01N 33/6893 |
| | | | 506/9 |
| 2014/0068489 A1 | 3/2014 | Wyland et al. | |
| 2014/0095186 A1 | 4/2014 | Gotz et al. | |
| 2014/0095201 A1* | 4/2014 | Farooq | G16H 50/30 |
| | | | 705/3 |
| 2014/0358576 A1* | 12/2014 | Hoffman | G16H 50/30 |
| | | | 705/2 |
| 2015/0025329 A1* | 1/2015 | Amarasingham | G06F 19/3456 |
| | | | 600/301 |
| 2015/0161331 A1 | 6/2015 | Oleynik | |
| 2015/0161346 A1 | 6/2015 | Hu et al. | |
| 2015/0213225 A1 | 7/2015 | Amarasingham et al. | |
| 2015/0220693 A1 | 8/2015 | Cadavid et al. | |
| 2015/0302241 A1* | 10/2015 | Eineren | A01J 5/007 |
| | | | 382/110 |
| 2015/0315652 A1 | 11/2015 | Rosenberg et al. | |
| 2015/0363553 A1 | 12/2015 | Rustgi et al. | |
| 2016/0063212 A1 | 3/2016 | Monier et al. | |
| 2016/0103967 A1 | 4/2016 | Bulut et al. | |
| 2016/0314256 A1 | 10/2016 | Su et al. | |
| 2017/0262587 A1 | 9/2017 | Agarwal et al. | |
| 2017/0344710 A1 | 11/2017 | Hu et al. | |

OTHER PUBLICATIONS

Disclosed Anonymously, "OptCare—A system for for personalizing clinical care pathways", IPCOM000244979D, Feb. 4, 2016, 13 pages.

* cited by examiner

MEDICAL SIDE EFFECTS TRACKING

BACKGROUND

1. Technical Field

Present invention embodiments relate to tracking medical side effects for a patient and, more specifically, analyzing medical information of patients and providing, to the patients, notifications of medical side effects that they could potentially experience.

2. Discussion of the Related Art

In the medical field, almost every treatment or medicine contains associated side effects that patients experience. For some patients, it is guaranteed or inevitable that certain side effects are inevitable or guaranteed to occur based on the medicine or treatment received. The type of side effects experienced by patients may vary greatly. For example, side effects can range from a mild fever or rash to a dangerous side effect that requires medical attention. In addition, the side effects experienced by different individuals may vary even though the individuals may be taking the same medication or receiving the same treatment.

Patients may routinely return to their doctors when experiencing side effects despite the fact that the side effect may not require medical attention from the doctor. Repeated unnecessary visits increases the costs incurred both by the patient and the medical offices.

SUMMARY

According to one embodiment of the present invention, a system for monitoring medical events for adverse effects includes at least one processor. The at least one processor may be configured to identify one or more medical events within the medical information of patients by applying a first analytics to the medical information. The medical information may include unstructured information. The processor is further configured to determine adverse effects of the identified medical events and corresponding time intervals of occurrence by applying second analytics to the medical reference information, wherein effect information includes the identified medical events, determined adverse effects, and corresponding time intervals of occurrence. In addition the processor is configured to determine from the effect information one or more adverse effects for a medical event of a patient and the corresponding time intervals of occurrence. Finally, the processor is configured to notify a user of the determined adverse effects prior to initiation of the corresponding time intervals of occurrence.

BRIEF DESCRIPTION OF THE DRAWINGS

Generally, like reference numerals in the various figures are utilized to designate like components.

Like reference numerals have been used to identify like elements throughout this disclosure.

DETAILED DESCRIPTION

The present invention embodiments pertain to a system and method for monitoring medical events for adverse side effects and notifying the patient of the possibility of the occurrence of an adverse side effect. The system utilizes text analytics (i.e., both-rules based and statistical) on patient medical information (e.g., medical records, doctor's notes, patient visits, patient profile statistics, etc.) to identify medical events and their dates. The system is capable of analyzing both structured and unstructured text from the patient medical information. The system also utilizes text analytics on medical reference information, or general medical knowledge, to identify potential side effects of the patients based on their patient medical information. The system may then build a timeline for the identified medical events and the identified potential side effects, where the timeline takes into account the time intervals of occurrence of the side effects. The system may further send a notification to a device indicating, prior to their occurrence, the identified potential side effect. Essentially, the system warns patients of the potential for a side effect associated with their medical events prior to the side effects being experienced.

Providing a system to track potential side effects and notify the patient of the possible occurrence and severity of a side effect can reducing the number of patient medical visits, which would reduce medical costs for both patients and medical offices. In addition, identifying potentially dangerous and severe side effects more quickly could have direct impact on the patient's overall treatment and health outcomes.

Figure 1:
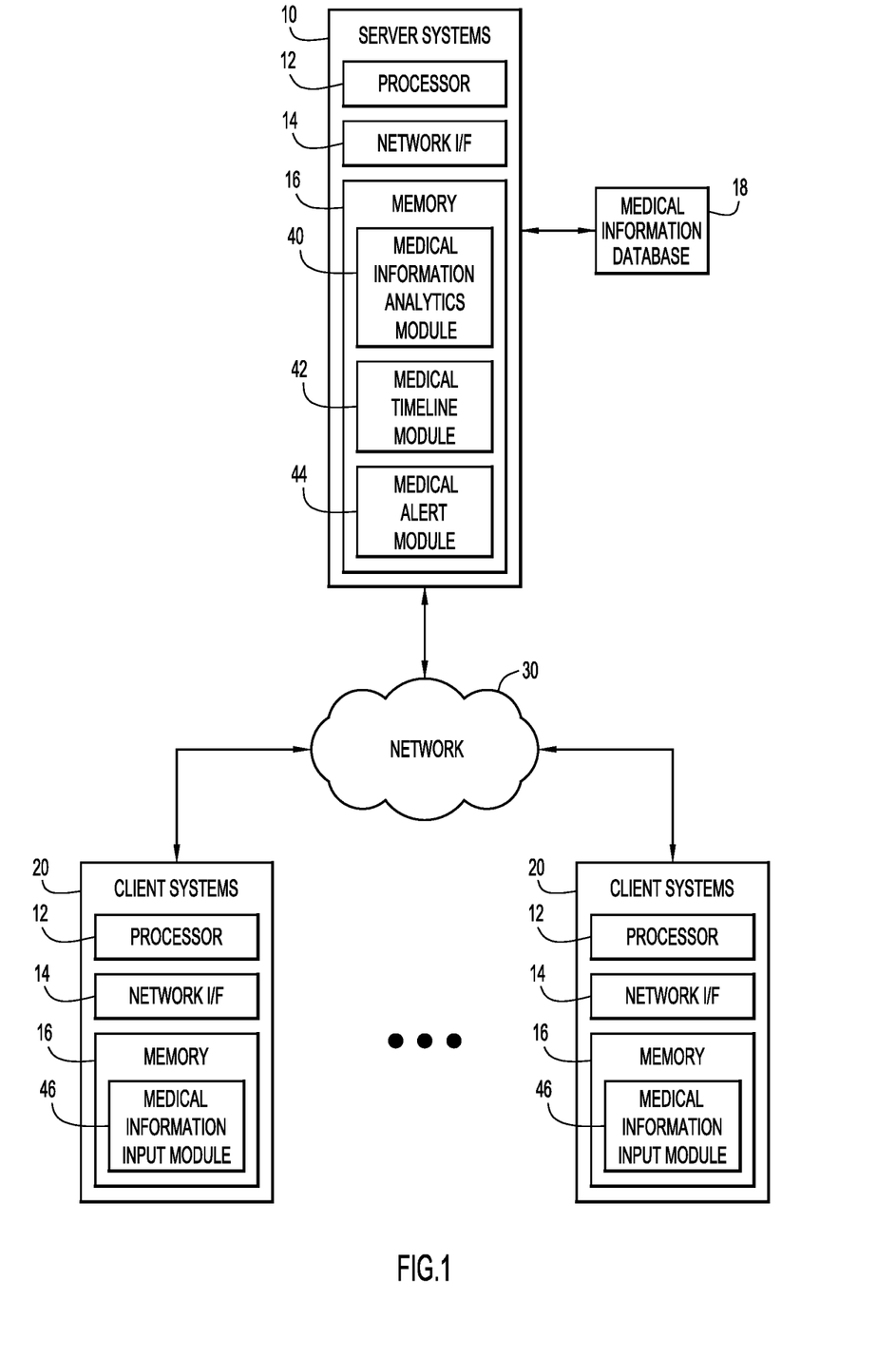
FIG. 1 is a diagrammatic illustration of an example of a computing environment for use with an embodiment of the present invention.

An example computing environment for use with present invention embodiments is illustrated in FIG. 1. Specifically, the computing environment includes one or more server systems 10, and one or more client systems 20. Server systems 10 and client systems 20 may be remote from each other and communicate over a network 30. The network may be implemented by any number of any suitable communications media (e.g., wide area network (WAN), local area network (LAN), Internet, Intranet, etc.). Alternatively, server systems 10 and client systems 20 may be local to each other, and communicate via any appropriate local communication medium (e.g., local area network (LAN), hardwire, wireless link, Intranet, etc.).

Server systems 10 may be implemented by any conventional or other computer systems preferably equipped with a display or monitor, a base (e.g., including at least one CPU or processor 12, one or more memories 16, and/or internal or external network interfaces or communications devices 14 (e.g., modem, network cards, etc.)), optional input devices (e.g., a keyboard, mouse or other input device), and any commercially available and custom software (e.g., server/communications software, medical information analytics module 40, medical timeline module 42, medical alert module 44, etc.).

Client systems 20 may be preferably equipped with at least one CPU or processor 12, one or more memories 16, internal or external network interfaces or communications devices 14 (e.g., transceiver, network cards, etc.)), and/or optional input or output devices (e.g., a keyboard, mouse or other input device, a display, etc.). The client systems 20 may further include any commercially available or custom software and/or hardware modules for the particular device to perform device operations (e.g., applications, browser, communications software, medical information input module 46, etc.). Client systems 20 may communicate with server systems 10 for uploading patient medical information, updating medical reference information, and determining potential adverse side effects of a patient.

Medical information input module 46 enables users of the client systems 20 to submit general medical information or medical reference information to server systems 10 for sets of data stored by the server systems 10 on the medical information database 18. These users may be medical professionals (doctors, nurses, technicians, etc.), medical researchers, etc. The medical reference information may include, but is not limited to, general medical knowledge known to those in the medical field and industry. This includes information published in medical journals, medical encyclopedias, medical textbooks, medical research, etc. The medical information input module 46 may also enable the server systems 10 to pull new or relevant medical reference information from client systems 20 to update the database 18 with the latest medical knowledge. Medical information input module 46 also enables users of the client systems 20 to submit patient medical information (e.g., patient medical records, doctor's notes, prescriptions, patient visits, etc.) to server systems 10 to be stored and analyzed by the server systems 10. The medical information input module 46 may also enable the server systems 10 to pull new or relevant patient medical information from the client systems 20 without requiring the users of the client systems 20 to upload the information to the server systems 10. These users may be the patient themselves, or may include other users such as, but not limited to, doctors of the patient, nurses associated with the doctors, and/or office personal that work in the office of the doctors. As further explained below, the medical information input module 46 may also enable a user of the client systems 20 to query the server systems 10 to determine if symptoms experienced by the user are a side effect of a recent medical event.

One or more databases 18 may store various types of information (e.g., patient medical information, medical reference information, etc.). The database 18 may be implemented by any conventional storage unit, may be local to, or remote from, server systems 10 and client systems 20, and may communicate via any appropriate communication medium (e.g., local area network (LAN), wide area network (WAN), Internet, hardwire, wireless link, Intranet, etc.). The client systems 20 may present a graphical user interface (e.g., GUI, etc.) or other type of interface (e.g., command line prompts, menu screens, etc.) to send data to the server systems 10, and may provide various types of information, including patient medical information and medical reference information.

The medical information analytics module 40 of the server systems 10 is configured to analyze both structured and unstructured text of the patient medical information to identify medical events, dates, and any other relevant data of the patient (i.e., patient profile statistics). As further explained below, this relevant information is utilized by the medical information analytics module 40 to determine if a patient has a likelihood of experiencing any potential adverse side effects as a result of any medications (i.e., current, past, and future medications), treatments, prior illnesses, etc. The medical information analytics module 40 compares and analyzes the relevant medical information of the patient medical information with the medical reference information stored in database 18 to identify the potential of any side effects of a patient and the corresponding time intervals of occurrence of the identified side effects.

The server systems 10 also include a medical timeline module 42. In the event that the medical information analytics module 40 determines that one or more side effects are probable for a patient, the medical timeline module 42 plots the time intervals of occurrence for the side effects (i.e., when the patient would experience the side effects, the duration in which each of the probable side effects would be experienced, etc.). The medical timeline module 42 may determine time interval ranges in which a side effect may occur and the duration of the side effect. The time intervals may be any amount of time including, but not limited to, seconds, minutes, hours, days, weeks, months, years, etc. The medical timeline module 42 may also have access to or be populated with the identified medical event dates from the patient medical information to enable the medical timeline module 42 to accurately determine and locate the time intervals of occurrence of any identified potential side effects.

The server systems 10 also include a medical alert module 44. The medical alert module 44 works with the medical timeline module 42 to send alerts to client systems 20 prior to a scheduled time interval of occurrence for a potential side effect. For example, if the medical timeline module 42 indicates that a patient may experience a side effect five days after receiving a treatment, the medical alert module 44 may, on the fourth day from the date of the treatment, send the client system 20 a notification that the patient may experience a certain side effect the next day. As previously explained, the users of the client systems 20 may be the patients themselves, or may include other users such as, but not limited to, doctors of a patient, nurses associated with the doctors, and/or office personal that work in the office of the doctors. Thus, the medical alert module 44 may send the notification to the client system 20 of the patient, or may send the notification to the client system 20 of a doctor's office of the patient, where the doctor's office could notify the patient that they may experience a side effect from a recent treatment received. As further explained below, the medical alert module 44 may be an active alert system or a passive alert system.

Modules 40, 42, 44, 46 may include one or more modules or units to perform the various functions of the present invention embodiments described below. The various modules (e.g., medical information analytics module 40, medical timeline module 42, medical alert module 44, medical information input module 46, etc.) may be implemented by any combination of any quantity of software and/or hardware modules or units, and may reside within memory 16 of the server system 10 and/or client systems 20 for execution by processor 12.

Figure 2:
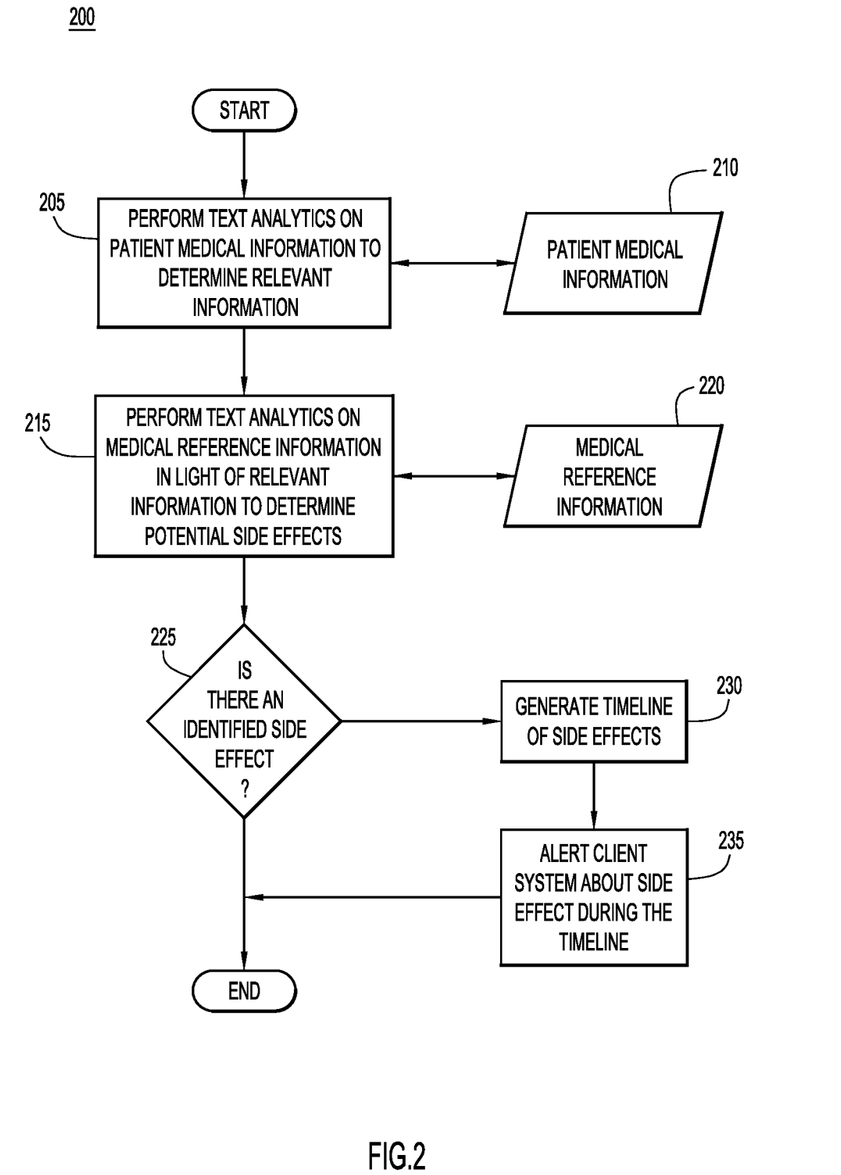
FIG. 2 is a procedural flow chart illustrating an example manner for monitoring medical events for adverse effects according to an embodiment of the present invention.

Turning to FIG. 2, illustrated is a flow chart 200 of the steps performed for analyzing and monitoring medical events to determine the possibility of adverse side effects of a patient. The flow chart 200 illustrated in FIG. 2 may be performed by the multiple devices (e.g., server system 10 and client systems 20) illustrated in FIG. 1 to operate the modules 40, 42, 44, and 46 to detect medical events and other relevant medical information in the patient medical information, analyze the medical events and the relevant medical information in light of the medical reference information, determine the possibility that the patient will experience an adverse side effect, and notify the patient when any determined adverse side effects may occur. At block 205, the medical information analytics module 40 may perform text analytics on the patient medical information of block 210. The patient medical information of block 210 may include, but is not limited to, patient profile statistics, patient medical records, doctor's notes, prescriptions, etc. The patient medical information may be uploaded to the server system 10 from the client system 20 via the medical information input module 46, or may be pulled from the client systems 20 by the server systems 10 via the medical information input module 46. The patient medical information of block 210 may be in both a structured format and an unstructured format. The medical information analytics module 40 may utilize rules-based and/or statistical text analytics to analyze the unstructured text of the patient medical information to acquire and extract relevant information. The medical information analytics module 40 may also utilize the structured information and data of the patient medical information to acquire and extract relevant information. Relevant medical information may include, but is not limited to medical events (e.g., treatments, symptoms experienced, etc.), patient profile statistics (e.g., height, weight, gender, ethnicity, blood type, blood pressure, cholesterol, etc.), medication names, etc.

At block 215, the medical information analytics module 40 may perform text analytics on the medical reference information of block 220 in light of the relevant information acquired in block 205 from the patient medical information of block 210. The medical information analytics module 40 may acquire the medical reference information from the database 18, or may query client systems 20 for medical reference information updates. Similar to the patient medical information of block 210, the medical reference information 220 may be formatted both in an unstructured and a structured format. Thus, the medical information analytics module 40 may utilize rules-based and/or statistical text analytics of the unstructured text of the medical reference information of block 220 to determine if, based on the relevant information extracted at block 205, that the patient may experience a side effect in the future. In addition, the medical information analytics module 40 may also utilize any structured information of the medical reference information of block 220 to determine if, based on the relevant information extracted at block 205, that the patient may experience a side effect in the future. The medical information analytics module 40 may also analyze the medical reference information of block 220 to determine the time intervals of occurrence for each of the identified side effects.

At block 225, the medical information analytics module 40 determines whether or not a patient, based on the analysis of the patient medical information of block 210 and the analysis of the medical reference information of block 220, is likely to experience some type of adverse side effect. As previously explained, the adverse side effect may be a result of medication being taken, a procedure that was performed on the patient, a disease that the patient has been previously diagnosed with, etc., where this information was discovered by the medical information analytics module 40 at block 205 when performing text analytics on the patient medical information of block 210. If, at block 225, a potential adverse side effect is identified, then, at block 230, the medical timeline module 42 generates or builds a timeline of the identified potential adverse side effects and of the medical event or events that may have triggered the adverse side effects (i.e., the time intervals of occurrence for each identified potential adverse side effect, the time intervals between each identified potential adverse side effect and the corresponding medical event, etc.). The medical timeline module 42 also, at block 230 tracks the current date and/or time in view of the medical event and the timeline of the potential adverse side effects (i.e., the time interval between the current date and the scheduled time interval of occurrence for each identified potential adverse side effect).

When the current date and/or time at block 230 indicates that a potential adverse side effect could soon be experienced by the patient (i.e., within a day, within an hour, etc.), then, at block 235, the medical alert module 44 sends a notification to at least one of the client systems 20 prior to the initiation of the corresponding time interval of the adverse side effect. The notification may inform the user of the client system 20 the type of adverse side effect, the symptoms of the adverse side effect, the duration or time interval of the adverse side effects, the medical event in connection with the adverse side effect, etc. As previously explained, the client system 20 may be a device of the patient themselves, or may be a device of the office of the doctor associated with the medical event connected to the adverse side effect.

Figure 3:
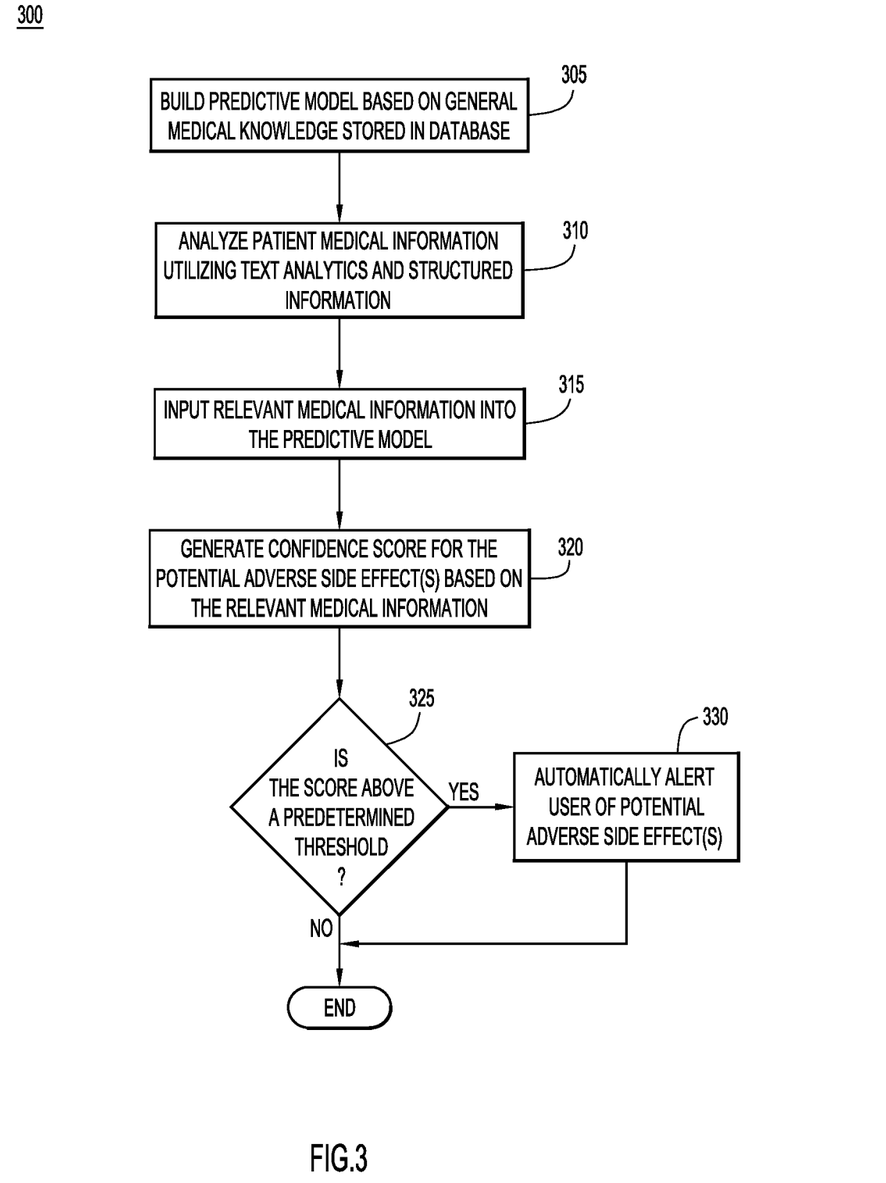
FIG. 3 is a procedural flowchart illustrating an example of an active alert system according to an embodiment of the present invention.

Turning to FIG. 3, illustrated is a flow chart 300 of the steps performed for actively notifying a user of a client system 20 of an identified potential adverse side effect. The flow chart 300 illustrated in FIG. 3 may be performed by the multiple devices (e.g., server system 10 and client systems 20) illustrated in FIG. 1 to operate the modules 40, 42, 44, and 46 to detect medical events and other relevant medical information in the patient medical information, analyze the medical events and the relevant medical information in light of the medical reference information, and actively notify a user when any determined adverse side effects may occur. At block 305, the medical information analytics module 40 may use text analytics to analyze the medical reference information to build a predictive or statistical model. As previously explained, the medical information analytics module 40 may acquire the medical reference information when it is stored in the database 18, or may query client systems 20 for medical information updates to the medical reference information. The medical reference information may be formatted in an unstructured and structured format, where the medical information analytics module 40 may utilize rules-based and/or statistical text analytics to analyze the unstructured text of the medical reference information and acquire data from the unstructured text. The medical information analytics module 40 may utilize any structured information of the medical reference information in combination with the data acquired from analyzing the unstructured information to build the predictive model.

At block 310, the medical information analytics module 40 may perform text analytics on the patient medical information (e.g., patient profile statistics, patient medical records, doctor's notes, prescriptions, etc.) for a patient. As previously explained, the patient medical information may be in both a structured format and an unstructured format, where the medical information analytics module 40 may utilize rules-based and/or statistical text analytics to acquire and extract relevant information from the unstructured information of the patient medical information. The medical information analytics module 40 may also utilize the structured information and data of the patient medical information do acquire and extract relevant information.

At block 315, once the relevant information has been extracted from the patient medical information, the medical information analytics module 40 inputs the relevant information into the predictive model. At block 320, the predictive model analyzes the relevant information to generate a confidence score, percentage, or ratio representing the likelihood the patient would experience any potential adverse side effects. For example, the relevant information extracted from the patient medical information may include, but is not limited to, the patient's profile statistics, medications currently being taken, treatments received in the past and adverse side effects experienced from those treatments, recent treatments, etc. This relevant information may be inserted into the predictive model, where the predictive model provides a confidence score for each potential adverse side effects the patient may possibly experience as a result of their relevant information.

At block 325, the medical information analytics module 40 determines if any of the potential adverse side effects contained a confidence score above a predetermined threshold. The threshold may be set by a user of a client system 20 (e.g., the patient themselves, the patient's doctor, etc.), or may be calculated by the medical information analytics module 40. For example, the medical information analytics module 40 may determine that confidence scores above a certain threshold are more likely than not to be experienced by the patient. If, at block 325, the medical information analytics module 40 determines that an identified potential adverse side effect does not contain a confidence score above the predetermined threshold, then the medical information analytics module 40 does not notify the client system 20 of the adverse side effect.

However, if, at block 325, the medical information analytics module 40 determines that an identified potential adverse side effect does contain a confidence score above the predetermined threshold, then the medical alert module 44 automatically sends a notification of the client system 20. In accordance with the example embodiment of FIG. 2, if any identified potential adverse side effects do contain a confidence score above the predetermined threshold, the medical timeline module 42 may generate or build a timeline of the identified potential adverse side effects and of the medical event or events that triggered the identified potential adverse side effects. The medical alert module 44 will automatically send a notification to the client system(s) 20 prior to the scheduled time interval of occurrence for the identified potential adverse side effects. The notification sent by the medical alert module 44 may be in the form of any message, including, but not limited to, an SMS text message, an email, a software bot, a software application, an in-application statement, a voice message, a pop-up message, etc. The medical alert module 44 may send the notification to the client system 20 based on the timeline created by the medical timeline module 42.

Figure 4:
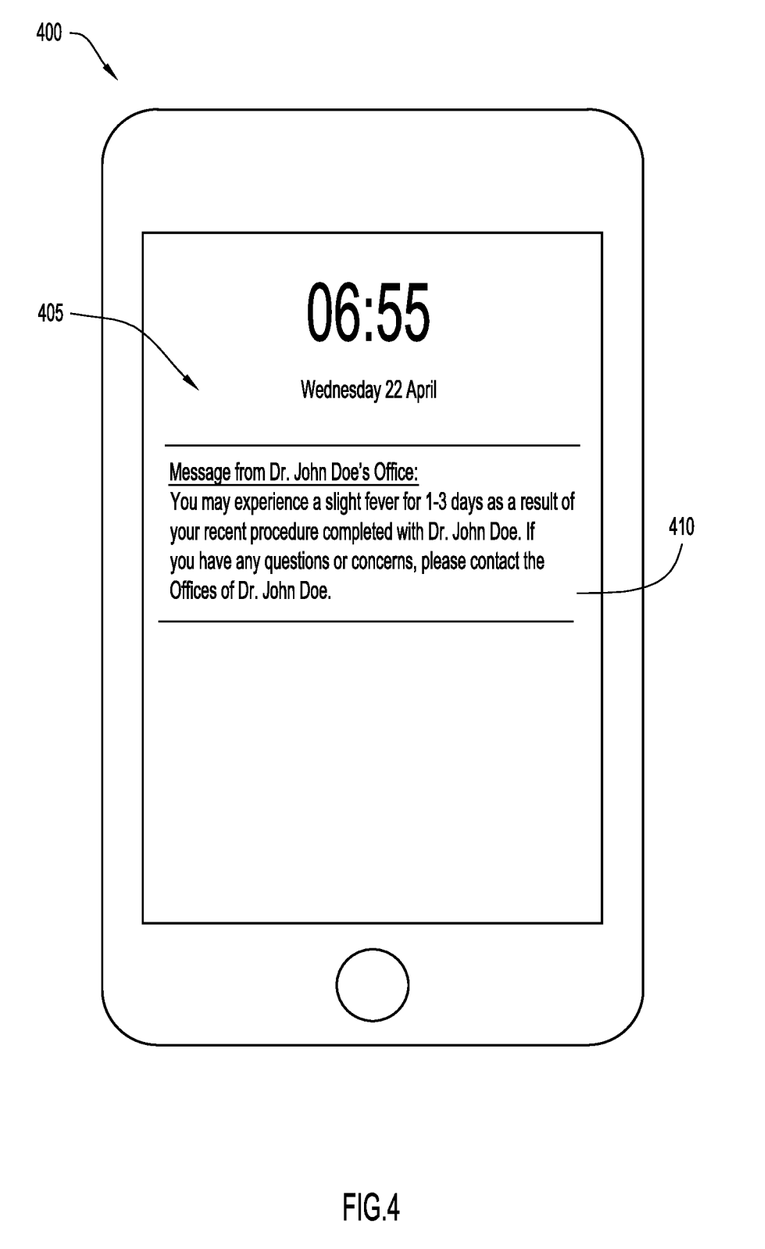
FIG. 4 is an example of the notification displayed on a mobile device according to an embodiment of the present invention.

FIG. 4 illustrates a client system 20 in the form of a mobile electronic device 400, where the mobile electronic device belongs to a patient. As illustrated, the mobile electronic device 400 includes a screen 405. When the mobile electronic device 400 receives a notification 410 from the medical alert module 44 of the server system 10, the mobile electronic device 400 may display the notification 410 on the screen 405 such that it is visible to the user (e.g., the patient) of the mobile electronic device 400. As illustrated in FIG. 4, the notification 410 may indicate to the user, the adverse side effect (e.g., fever) and the duration of the adverse side effect (e.g., 1-3 days).

Figure 5:
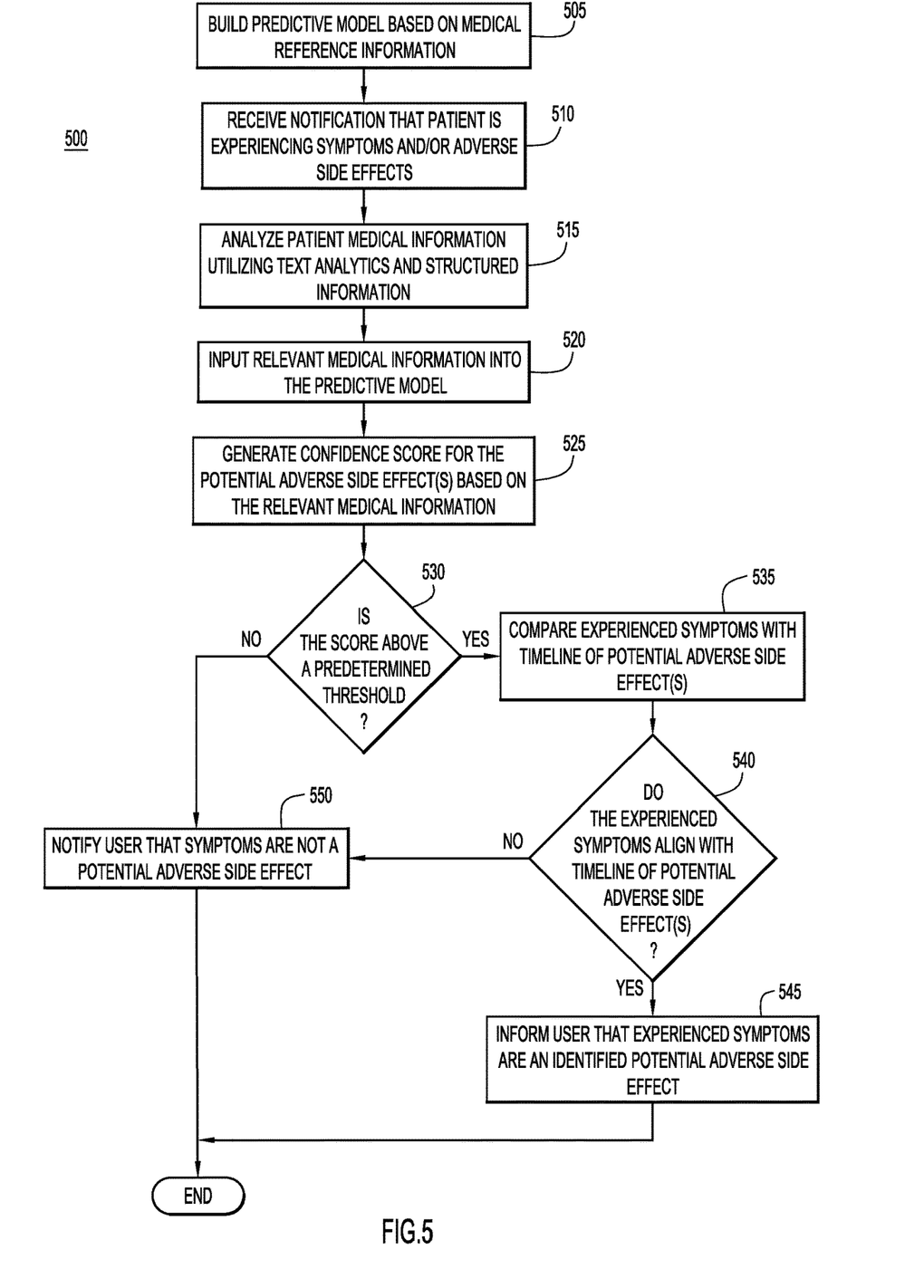
FIG. 5 is a procedural flow chart illustrating an example of a passive alert system according to an embodiment of the present invention.

Turning to FIG. 5, illustrated is a flow chart 500 of the steps performed for passively notifying a user of a client system 20 of a potential adverse side effect. The flow chart 500 illustrated in FIG. 5 may be performed by the multiple devices (e.g., server system 10 and client systems 20) illustrated in FIG. 1 to operate the modules 40, 42, 44, and 46 to detect medical events and other relevant medical information in the patient medical information, analyze the medical events and the relevant medical information in light of the medical reference information, and passively notify a user of the adverse side effects when inquired by from the user. At block 505, the medical information analytics module 40 may use text analytics to analyze the medical reference information to build a predictive or statistical model. Similar to the example embodiment illustrated in FIG. 3, the medical information analytics module 40 may acquire the medical reference information when it is stored in the database 18, or may query client systems 20 for medical information updates to the medical reference information. The medical reference information may be formatted in an unstructured and structured format, where the medical information analytics module 40 may utilize rules-based and/or statistical text analytics to analyze the unstructured text of the medical reference information and acquire data from the unstructured text. The medical information analytics module 40 may utilize any structured information of the medical reference information in combination of the data acquired from analyzing the unstructured information to build the predictive model. Some examples of the type of predictive models include, but are not limited to, a naive Bayes classifiers model, an ordinary least squares model, a multivariate adaptive regression splines model, a neural network model, etc.

At block 510, the user (e.g., patient, doctor, nurse, etc.) of a client system 20 may notify the server system 10 that the patient is experiencing medical symptoms or some type of side effect. The client system 20 may send the notification and the type of symptoms or effects the patient is experiencing through the medical information input module 46 of the client systems 20.

At block 515, in response to receiving the notification of the patient at block 510, the medical information analytics module 40 of the server system 10 may perform text analytics on the patient medical information (e.g., patient profile statistics, patient medical records, doctor's notes, prescriptions, etc.) for that patient. As previously explained, the patient medical information may have already been uploaded previously to the server systems 10, or the server systems 10 may request or pull the latest patient medical information from the client systems 20. The patient medical information may be in both a structured format and an unstructured format, where the medical information analytics module 40 may utilize rules-based and/or statistical text analytics to acquire and extract relevant information from the unstructured information of the patient medical information. The medical information analytics module 40 may also utilize the structured information and data of the patient medical information to acquire and extract relevant information.

At block 520, once the relevant information has been extracted from the patient medical information, the medical information analytics module 40 inputs the relevant information into the predictive model. At block 525, the predictive model analyzes the relevant information to generate a confidence score, percentage, or ratio representing the likelihood the patient would experience any potential adverse side effects. For example, the relevant information extracted from the patient medical information may include, but is not limited to, the current symptoms and side effects reported by the patient, the patient's profile statistics, medications currently being taken, treatments received in the past and adverse side effects experienced from those treatments, recent treatments, etc. This relevant information may be inserted into the predictive model, where the predictive model provides a confidence score for each adverse side effects the patient may possibly experience as a result of their relevant information.

At block 530, the medical information analytics module 40 determines if any of the identified potential adverse side effects contained a confidence score above a predetermined threshold. Similar to the example embodiment illustrated in FIG. 3, the threshold may be set by a user of a client system 20 (e.g., the patient themselves, the patient's doctor, etc.), or may be calculated by the medical information analytics module 40. For example, the medical information analytics module 40 may determine that confidence scores above a certain threshold are more likely than not to be experienced by the patient.

If, at block 530, the medical information analytics module 40 determines that any identified potential adverse side effects do contain a confidence score above the predetermined threshold, then the medical timeline module 42, at block 535 compares the scheduled time interval of occurrence for each of the identified potential adverse side effects having a high enough confidence score with the current date, or the date in which the notification about the patient was received. At block 540, the medical timeline module 42 then determines whether the symptoms experienced by the patient align within the time period of the identified potential adverse side effects. If at block 540, the medical timeline module 42 determines that the experienced symptoms do align with at least one of the identified potential side effects, the medical alert module 44, may, at block 545 send a notification of the adverse side effect to the client system 20 that submitted the query at block 510. However, if, at block 540, the medical timeline module 42 determines that the experienced symptoms do not align along the timeline with at least one of the identified potential side effects, the medical alert module 44, may, at block 550, send a notification to the client system 20 that the symptoms experienced by the patient are not an identified side effect in accordance with the patient medical information.

Returning to block 530, if the medical information analytics module 40 determines that any identified potential adverse side effects do not contain a confidence score above the predetermined threshold, then the medical alert module 44 may send a notification to the client system 20 that originated the query in block 510 that the symptoms experienced by the patient may not be an identified side effect in accordance with the patient medical information.

In one example embodiment in accordance with FIG. 5, the patient may send the query of block 510 to the server system 10 via an application running on their client system 20 by way of the medical information input module 46, and the notification received regarding whether or not the experienced symptoms are an identified side effect of the medical history of the patient is received in the application of the client system 20. In other example embodiments, the notification sent by the medical alert module 44 may be in the form of any message, including, but not limited to, an SMS text message, an email, a software bot, a software application, an in-application statement, a voice message, a pop-up message, etc., where the notification is sent in response to receiving the query from the client system 20 in block 510.

It will be appreciated that the embodiments described above and illustrated in the drawings represent only a few of the many ways of implementing embodiments for monitoring medical events for adverse effects.

The embodiments described above and illustrated in the drawings improve medical outcomes while decreasing medical costs to the medical industry. The embodiments described above may prevent repeated trips to the doctor by patients experiencing temporary and typical side effects that are of no minor significance. The embodiments described above, may also enable a patient to identify when they are not experiencing a potential side effect from a treatment received or medications taken, which can prompt the patient to seek immediate medical attention.

In some embodiments, the client systems 20 may be equipped with sensors that measure abnormal physiological conditions of a user (e.g., patient) of the client system 20. The sensors may be in communication with the medical information input module of the client systems 20 to enable the conditions to be sent to the server system 10, where the server system 20 can analyze the conditions in conjunction with the user's patient medical information to determine any potential adverse side effects. In addition, in the embodiments described above, the medical alert module 44 may determine the best available message system in which to send a notification to the client systems 20. The medical alert module 44 may utilize user personal preferences, the time of day, the severity of the adverse side effect, and other factors, for determining the type of message system in which to send the notification to the client system 20. For example, the medical alert module 44 may be triggered in the middle of the night to send a notification regarding a non-life threatening adverse side effect, and would determine that email may be a more suitable type of message system than that of an SMS message. Furthermore, in the embodiments described above, the medical alert module 44 may further utilize a set of factors (e.g., user personal preferences, the severity of the adverse side effect, etc.) for determining the client systems 20 in which to send a notification. For example, more severe adverse side effects may be sent to both the client system 20 of the patient and the client system 20 of the doctor of the patient.

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, medical information analytics module, medical timeline module, medical alert module, medical information input module, etc.). These systems may include any types of monitors and input devices (e.g., keyboard, mouse, voice recognition, etc.) to enter and/or view information.

It is to be understood that the software (e.g., medical information analytics module, medical timeline module, medical alert module, medical information input module, etc.) of the present invention embodiments may be implemented in any desired computer language and could be developed by one of ordinary skill in the computer arts based on the functional descriptions contained in the specification and flow charts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and communicate via any suitable communications medium (e.g., LAN, WAN, Intranet, Internet, hardwire, modem connection, wireless, etc.). For example, the functions of the present invention embodiments may be distributed in any manner among the various end-user/client and server systems, and/or any other intermediary processing devices. The software and/or algorithms described above and illustrated in the flow charts may be modified in any manner that accomplishes the functions described herein. In addition, the functions in the flow charts or description may be performed in any order that accomplishes a desired operation.

The software of the present invention embodiments (e.g., medical information analytics module, medical timeline module, medical alert module, medical information input module, etc.) may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information (e.g., patient medical information, medical reference information, etc.). The database system may be implemented by any number of any conventional or other databases, data stores or storage structures (e.g., files, databases, data structures, data or other repositories, etc.) to store information (e.g., patient medical information, medical reference information, etc.). The database system may be included within or coupled to the server and/or client systems. The database systems and/or storage structures may be remote from or local to the computer or other processing systems, and may store any desired data (e.g., patient medical information, medical reference information, etc.).

The present invention embodiments may employ any number of any type of user interface (e.g., Graphical User Interface (GUI), command-line, prompt, etc.) for obtaining or providing information (e.g., patient medical information, medical reference information, etc.), where the interface may include any information arranged in any fashion. The interface may include any number of any types of input or actuation mechanisms (e.g., buttons, icons, fields, boxes, links, etc.) disposed at any locations to enter/display information and initiate desired actions via any suitable input devices (e.g., mouse, keyboard, etc.). The interface screens may include any suitable actuators (e.g., links, tabs, etc.) to navigate between the screens in any fashion.

The present invention embodiments are not limited to the specific tasks or algorithms described above, but may be utilized for monitoring medical events for adverse side effects by analyzing patient medical information and medical reference information.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method of monitoring medical events for adverse effects comprising:
   identifying one or more medical events within medical information of a patient by applying first analytics to the medical information, wherein the medical information includes unstructured information;
   determining potential adverse effects of the identified medical events and corresponding time intervals of occurrence by applying second analytics to medical reference information, wherein effect information includes the identified medical events, determined potential adverse effects, and corresponding time intervals of occurrence;
   determining from the effect information one or more adverse effects for a medical event of the patient and the corresponding time intervals of occurrence, wherein determining the one or more adverse effects includes:
      generating a confidence score for each of the determined potential adverse effects;
      determining the one or more adverse effects from the determined potential adverse effects based on the confidence score for the determined potential adverse effects satisfying a threshold; and generating a timeline of the determined one or more adverse effects, wherein the timeline indicates the corresponding time intervals of occurrence for each of the determined one or more adverse effects and time intervals between each of the determined one or more adverse effects and the medical event of the patient; and notifying a user of the determined one or more adverse effects prior to initiation of the corresponding time intervals of occurrence based on alignment of conditions of the patient with the timeline.

2. The method of claim 1, wherein the unstructured information comprises one or more from a group of medical records, medical notes, and information pertaining to visits to medical facilities.

3. The method of claim 1, wherein the one or more medical events include one or more from a group of a medical procedure and a medical treatment.

4. The method of claim 1, wherein the first and second analytics include one or more from a group of rule-based analytics and statistical analytics.

5. The method of claim 1, wherein the medical reference information includes patient profile statistics.

6. The method of claim 1, wherein determining the one or more adverse effects comprises:

generating a confidence score for each of the determined potential adverse effects via a predictive model.

7. A system for monitoring medical events for adverse effects comprising:

at least one processor configured to:
identify one or more medical events within medical information of a patient by applying first analytics to the medical information, wherein the medical information includes unstructured information;
determine potential adverse effects of the identified medical events and corresponding time intervals of occurrence by applying second analytics to medical reference information, wherein effect information includes the identified medical events, determined potential adverse effects, and corresponding time intervals of occurrence;
determine from the effect information one or more adverse effects for a medical event of the patient and the corresponding time intervals of occurrence, wherein determining the one or more adverse effects includes:
generating a confidence score for each of the determined potential adverse effects;
determining the one or more adverse effects from the determined potential adverse effects based on the confidence score for the determined potential adverse effects satisfying a threshold; and
generating a timeline of the determined one or more adverse effects, wherein the timeline indicates the corresponding time intervals of occurrence for each of the determined one or more adverse effects and time intervals between each of the determined one or more adverse effects and the medical event of the patient; and
notify a user of the determined one or more adverse effects prior to initiation of the corresponding time intervals of occurrence based on alignment of conditions of the patient with the timeline.

8. The system of claim 7, wherein the unstructured information comprises one or more from a group of medical records, medical notes, and information pertaining to visits to medical facilities.

9. The system of claim 7, wherein the one or more medical events include one or more from a group of a medical procedure and a medical treatment, and wherein the medical reference information includes patient profile statistics.

10. The system of claim 7, wherein the first and second analytics include one or more from a group of rule-based analytics and statistical analytics.

11. The system of claim 7, wherein determining the one or more adverse effects further comprises:

generating a confidence score for each of the determined potential adverse effects via a predictive model.

12. A computer program product for monitoring medical events for adverse effects comprising:

one or more computer readable storage media collectively having program instructions embodied therewith, the program instructions executable by a processor to cause the processor to:
identify one or more medical events within medical information of a patient by applying first analytics to the medical information, wherein the medical information includes unstructured information;
determine potential adverse effects of the identified medical events and corresponding time intervals of occurrence by applying second analytics to medical reference information, wherein effect information includes the identified medical events, determined potential adverse effects, and corresponding time intervals of occurrence;
determine from the effect information one or more adverse effects for a medical event of the patient and the corresponding time intervals of occurrence, wherein determining the one or more adverse effects includes:
generating a confidence score for each of the determined potential adverse effects;
determining the one or more adverse effects from the determined potential adverse effects based on the confidence score for the determined potential adverse effects satisfying a threshold; and
generating a timeline of the determined one or more adverse effects, wherein the timeline indicates the corresponding time intervals of occurrence for each of the determined one or more adverse effects and time intervals between each of the determined one or more adverse effects and the medical event of the patient; and
notify a user of the determined one or more adverse effects prior to initiation of the corresponding time intervals of occurrence based on alignment of conditions of the patient with the timeline.

13. The computer program product of claim 12, wherein the unstructured information comprises one or more from a group of medical records, medical notes, and information pertaining to visits to medical facilities.

14. The computer program product of claim 12, wherein the one or more medical events include one or more from a group of a medical procedure and a medical treatment, and wherein the medical reference information includes patient profile statistics.

15. The computer program product of claim 12, wherein the first and second analytics include one or more from a group of rule-based analytics and statistical analytics.

16. The computer program product of claim 12, wherein determining the one or more adverse effects further comprises:
 generating a confidence score for each of the determined potential adverse effects via a predictive model.

\* \* \* \* \*